United States Patent
Renault

(10) Patent No.: US 6,562,355 B1
(45) Date of Patent: May 13, 2003

(54) COMIXTURE OF DEXTRAN SULFATE/ESCIN FOR TREATING SKIN REDNESS/EDEMA AND/OR SENSITIVE SKIN

(75) Inventor: Béatrice Renault, Saint Maurice (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/684,986

(22) Filed: Oct. 10, 2000

(30) Foreign Application Priority Data

Oct. 8, 1999 (FR) .............................. 99 12589

(51) Int. Cl.$^7$ .......................... A61K 6/00; A61K 9/127; A61K 9/14; A61K 7/06; A61K 7/32
(52) U.S. Cl. .......................... 424/401; 424/45; 424/63; 424/70.1; 424/70.11; 424/70.13; 424/450; 424/489; 424/65
(58) Field of Search .............................. 424/70.1, 70.11, 424/70.13, 401, 450, 45, 63, 65, 489; 514/23, 871, 886

(56) References Cited

U.S. PATENT DOCUMENTS

| | | | |
|---|---|---|---|
| 4,686,211 A | * 8/1987 | Hara et al. ................... | 514/148 |
| 5,100,879 A | * 3/1992 | Ueno et al. ................... | 514/59 |
| 5,145,686 A | * 9/1992 | Horrobin et al. ............ | 424/677 |
| 5,587,295 A | * 12/1996 | Lopukhin et al. ............. | 435/11 |
| 5,631,011 A | * 5/1997 | Wadstrom ................... | 424/400 |
| 5,719,197 A | * 2/1998 | Kanios et al. | |
| 5,728,683 A | * 3/1998 | Maeda et al. ................. | 514/33 |
| 5,879,688 A | * 3/1999 | Coury et al. ................ | 424/401 |
| 6,147,054 A | * 11/2000 | De Paoli Ambrosi ......... | 514/23 |
| 6,197,319 B1 | * 3/2001 | Wang et al. ................ | 424/401 |

FOREIGN PATENT DOCUMENTS

| | | |
|---|---|---|
| EP | 0 803 246 A1 | 10/1997 |
| FR | 2 047 874 A | 3/1971 |
| FR | 2668061 A | * 10/1990 |
| FR | 2 668 061 A1 | 4/1992 |
| FR | 2 755 012 A1 | 4/1998 |

OTHER PUBLICATIONS

Derwent Information LTD, Chabrecek et al. Apr. 28, 2001.*

* cited by examiner

Primary Examiner—Thurman K. Page
Assistant Examiner—S. Tran
(74) Attorney, Agent, or Firm—Burns, Doane, Swecker & Mathis, L.L.P.

(57) ABSTRACT

Comixtures of escin and dextran sulfate are effective for treating skin redness/edema and/or sensitive skin, particularly redness and/or edema around the eyes and most particularly bags and/or dark rings around the eyes.

14 Claims, No Drawings

COMIXTURE OF DEXTRAN SULFATE/ ESCIN FOR TREATING SKIN REDNESS/ EDEMA AND/OR SENSITIVE SKIN

CROSS-REFERENCE TO PRIORITY APPLICATION

This application claims priority under 35 U.S.C. §119 of FR-99/12589, filed Oct. 8, 1999, hereby expressly incorporated by reference.

BACKGROUND OF THE INVENTION

1. Technical Field of the Invention

The present invention relates to comixtures of dextran sulfate and escin for preventively or curatively treating skin redness and/or skin edema and/or sensitive skin, particularly redness and/or edema around the eyes and most particularly bags and/or dark rings around the eyes.

2. Description of the Prior Art

The human body in general is sensitive to the external attacking factors or challenges of modern life (exposure to UV radiation, large variations in hygrometry and temperature, pollution, etc.). The response to these challenges may be reflected, inter alia, by the appearance of redness associated with a local vasodilation or by the appearance of local edema.

In the field of skin disorders, it is known that certain skin types are more sensitive than others to external attacking factors.

The assignee hereof has now determined that the symptoms associated with sensitive skin are, in particular, subjective signs, which are essentially dysaesthetic sensations. By the expression "dysaesthetic sensations" are intended more or less painful sensations experienced in an area of skin, such as stinging, tingling, itching or pruritus, burning, heating, discomfort, tautness, etc., in response to various factors such as the environment, the emotions, foods, the wind, friction, shaving, soap, surfactants, hard water having a high calcium concentration, temperature variations, or wool.

Due to its structure and its high innervation, the area around the eyes is an anatomical region which is particularly sensitive to attacking factors or to behavioral mechanical stresses (friction). Following these stimuli and on account of a very low internal threshold of neurogenic sensitivity in certain more sensitive individuals, the area around the eyes rapidly shows evidence by redness and/or itching, which are the consequences of an exacerbated vasodilation, of a passing discomfort, but also by bags and/or dark rings and/or edema, of more persistent discomfort reflecting a greater metabolic depletion of the epidermis and the dermis.

Other than these physiological data, it is known that simply from their cosmetic appearance, redness, dark rings and bags have always been considered as unattractive and need continues to exist for means to mask or even eliminate same.

SUMMARY OF THE INVENTION

It has now surprisingly and unexpectedly been determined that comixture of dextran sulfate and escin elicits noteworthy calmant and/or vasodilation-inhibitory and/or anti-edema properties, these properties being developed in proportions which exceed the simple cumulation of the effects obtained with each of the components taken individually.

DETAILED DESCRIPTION OF BEST MODE AND SPECIFIC/PREFERRED EMBODIMENTS OF THE INVENTION

More particularly according to the present invention, dextran is a neutral polysaccharide with no charged moieties, which is biologically inert, and which is prepared by fermenting beet sugar containing only hydroxyl groups. It is possible to obtain dextran fractions of different molecular weights from native dextran by hydrolysis and purification. Too, dextran can be in the form of dextran sulfate.

Other than the physicochemical properties of dextran sulfate which are known to this art and which make it a good compound for cosmetic compositions (good solubility in water and saline solutions, high stability in solutions of pH ranging from 4 to 10 at room temperature), it is also known that dextran sulfate has properties of water absorption, a protective effect against the damage induced by free radicals, particularly in topical application, stabilization of proteins or unstable species and substances, and moisturization on account of its excellent hydrophilic properties. Biological properties such as an anti-coagulant effect, an inhibitory effect on enzymes such as hyaluronidase, glucosidases, elastase or even thrombin, and antiviral activity are also known.

As regards the skin and skin protection, dextran sulfate is known for its anti-wrinkle, anti-inflammatory, anti-allergic and anti-aging properties and for its role in treating rough and flaky skin and in moisturization.

Escin is a chemical molecule consisting of glucuronic acid and two sugars (glucose-xylose) linked to an aglycone, deglucoescin which has a molecular weight of 1131.24. This is a molecule which exists, for example, in plant extracts, particularly in extracts of common horsechestnut. In the prior art, escin is described in weight-reducing compositions (FR-2,729,856, EP-034,153, WO-97/42928 and WO-98/15259), in compositions for promoting blood circulation (EP-158,090 and U.S. Pat. No. 4,983,626), in compositions for treating the skin such as anti-inflammatory agents (EP-728,472), for improving the cohesion between the dermis and the epidermis (WO-98/19664) and in skin-lightening cosmetic compositions (JP-07,076,512).

It is also known to the prior art to formulate escin in compositions for treating bags and wrinkles under the eyes (FR-2,668,061, U.S. Pat. No. 5,273,916 and U.S. Pat. No. 5,571,503).

However, to date it is believed that the surprising synergistic effect exhibited by the intimate admixture of escin and dextran sulfate on the inhibition of the vasodilation and/or the anti-edema effect and/or the soothing of sensitive skin was unknown to this art.

Thus, the present invention features a comixture comprising, as active agent, formulated into a physiologically acceptable medium, intimate immixture of dextran sulfate and escin.

By the expression "physiologically acceptable medium" is intended a medium which is compatible with the skin, mucous membranes, the nails and the hair.

According to the invention, the composition preferably comprises dextran sulfate, in the form of a sodium salt thereof.

According to the invention, the dextran sulfate has a molecular weight ranging from $2 \times 10^3$ to $5 \times 10^6$ and preferably from $5 \times 10^3$ to $10^5$.

Too, the dextran sulfate can be of any origin. The compositions of the invention preferably comprise dextran sulfate marketed by Pharmacia Biotech under the trademark Dextran sulfate 10 sodium salt®.

The compositions of the invention comprise escin which can be of synthetic or natural origin.

By the expression "synthetic origin" is intended escin, in pure form or in solution, irrespective of its concentration in said solution, obtained by chemical synthesis. The expression "natural origin" connotes escin, in pure form or in solution, irrespective of its concentration in said solution, obtained from a natural element such as, for example, a plant extract, particularly an extract of common horsechestnut.

According to the invention, the composition preferably comprises escin marketed by the company Indena under the trademark escin 3030000® or, alternatively, escin marketed by the company LEK under the trademark amorphous beta Aescin®.

The amounts of dextran sulfate and of escin formulated into the compositions of the invention obviously depend on the desired effect.

For example, the amount by weight of dextran sulfate which are included in the compositions of the invention advantageously range, for example, from 0.01% to 5% and preferably from 0.05% to 2% relative to the total weight of the composition.

To provide an order of magnitude, the amount by weight of escin formulated according to the invention advantageously constitutes from 0.005% to 5% relative to the total weight of the composition, preferably from 0.01% to 2% relative to the total weight of the composition.

In the compositions of the invention, the weight ratio between the dextran sulfate and the escin advantageously ranges from $2 \times 10^{-3}$ to $10^3$ and preferably from $25 \times 10^{-3}$ to 200.

Although they can be formulated for any application, the compositions of the invention are preferably formulated for topical application.

The compositions of the invention can be for cosmetic or dermatological applications. According to the invention, the composition is preferably a cosmetic composition and even more preferably a cosmetic composition for topical application.

The present invention thus features comixture of dextran sulfate and escin for preventively or curatively treating skin redness and/or skin edema and/or sensitive skin.

The clinical signs of sensitive skin are essentially subjective: stinging, tingling, pruritus, tautness and heating, and they are occasionally associated with erythema.

Too, this invention features compositions of dextran sulfate and escin for preventively or curatively treating stinging and/or tingling and/or pruritus and/or tautness and/or heating and/or erythema.

As indicated above, the area around the eyes is particularly sensitive to external attacking factors or influenced.

Accordingly, this invention also features comixtures of dextran sulfate and escin for preventively or curatively treating redness and/or edema around the eyes.

Similarly, this invention features compositions comprising comixture of dextran sulfate and escin for preventively or curatively treating bags and/or dark rings around the eyes.

The compositions according to the invention comprise a cosmetically acceptable support (vehicle, diluent or carrier), i.e., a support which is compatible with the skin, mucous membranes, the nails and the hair and which can be in any pharmaceutical form normally employed for topical application, in particular in the form of an aqueous, aqueous alcoholic or oily solution, an oil-in-water or water-in-oil or multiple emulsion, an aqueous or oily gel, a liquid, an ointment, pasty or solid anhydrous product, a dispersion of oil in an aqueous phase with the aid of spherules, it being possible for these spherules to be polymer nanoparticles such as nanospheres and nanocapsules or, more preferably, lipid vesicles of ionic and/or nonionic type.

Such compositions may be more or less fluid and may have the appearance of a white or colored cream, an ointment, a milk, a lotion, a serum, a paste or a mousse. Same can optionally be topically applied onto the skin in the form of an aerosol. Same can also be in solid form and, for example, be in the form of a stick. These can be used as a care product, as a cleansing product, as a makeup product or as simple deodorant product.

In known fashion, the compositions of the invention can also contain adjuvants and additives that are conventional in cosmetics and dermatology, such as hydrophilic or lipophilic gelling agents, hydrophilic or lipophilic active agents, preservatives, antioxidants, solvents, fragrances, fillers, UV-screening agents, pigments, colorants, chelating agents, odor absorbers and dyestuffs. The amounts of the various adjuvants and additives are those conventionally employed in the fields considered, and, for example, advantageously range from 0.01% to 20% relative to the total weight of the composition. Depending on their particular nature, these adjuvants and additives can be introduced into the fatty phase, into the aqueous phase, into the lipid vesicles and/or into the nanoparticles.

When the compositions of the invention are emulsions, the proportion of the fatty phase advantageously ranges from 5% to 80% by weight, and preferably from 5% to 50% by weight, relative to the total weight of the composition. The oils, emulsifiers and co-emulsifiers formulated into the composition in emulsion form are selected from among those conventionally included in the field considered. The emulsifier and co-emulsifier are advantageously present in the composition in a proportion ranging from 0.3% to 30% by weight, and preferably from 0.5% to 20% by weight, relative to the total weight of the composition.

Exemplary oils according to the invention include mineral oils, oils of plant origin (apricot oil, sunflower oil), oils of animal origin, synthetic oils, silicone oils and fluoro oils (perfluoropolyethers). Fatty alcohols (cetyl alcohol), fatty acids and waxes (beeswax) are also representative fatty substances.

Exemplary emulsifiers and co-emulsifiers suited for the invention include fatty acid esters of polyethylene glycols such as PEG-40 stearate and PEG-100 stearate, and fatty acid esters of polyols, such as glyceryl stearate and sorbitan tristearate.

Exemplary hydrophilic gelling agents include, in particular, carboxyvinyl polymers (carbomer), acrylic copolymers such as acrylate/-alkylacrylate copolymers, polyacrylamides, polysaccharides, natural gums and clays, and exemplary lipophilic gelling agents include the modified clays such as bentones, metal salts of fatty acids, hydrophobic silica and polyethylenes.

The subject compositions can also contain other hydrophilic active agents, such as proteins or protein hydrolysates, amino acids, polyols, urea, allantoin, sugars and sugar derivatives, water-soluble vitamins, plant extracts and hydroxy acids.

And exemplary lipophilic active agents include retinol (vitamin A) and derivatives thereof, tocopherol (vitamin E) and derivatives thereof, essential fatty acids, ceramides, essential oils, and salicylic acid and derivatives thereof.

It is also envisaged to formulate into use in the composition of the invention, in addition to the escin/dextran sulfate comixture, compounds or species selected from among:

(a) plant hormones;

(b) calcium antagonists, such as verapamil and Diltiazem;

(c) OH-radical scavengers, such as dimethyl sulfoxide;

(d) chlorine-channel openers;

(e) plant extracts such as those from Iridacea and Rosacea plants or from soybean, these extracts possibly containing isoflavones;

(f) extracts of microorganisms including, in particular, bacterial extracts such as those of non-photosynthetic filamentous bacteria.

Other compounds or species can also be included in the above list, for example, potassium-channel openers such a diazoxide and minoxidil, spiroxazone, phospholipids such as lecithin, linoleic acid, linolenic acid, salicylic acid and derivatives thereof described in FR-2,581,542, such as salicylic acid derivatives bearing an alkyl group having from 2 to 12 carbon atoms in position 5 of the benzene ring, hydroxycarboxylic acids or keto carboxylic acids and their esters, lactones and their corresponding salts, anthralin, carotenoids, eicosatetraenoic acid and eicosatrienoic acid or their esters and amides, and vitamin D and its derivatives thereof.

In another embodiment of the invention, other active agents suited, in particular, for preventing and/or treating skin complaints or afflictions can be formulated into the subject compositions. Exemplary such active agents include:

(i) agents which modify skin differentiation and/or proliferation and/or pigmentation, such as retinoic acid and its isomers, retinol and its esters, vitamin D and its derivatives, estrogens such as estradiol, kojic acid or hydroquinone;

(ii) antibacterial agents such as clindamycin phosphate, erythromycin or antibiotics of the tetracycline class;

(iii) agents which modify the adhesion of bacteria to the skin and/or mucous membranes, such as honey, in particular acacia honey and certain sugar derivatives;

(iv) anti-parasitic agents, in particular metronidazole, crotamiton or pyrethroids;

(v) antifungal agents, in particular compounds belonging to the imidazole class such as econazole, ketoconazole or miconazole or their salts, polyene compounds such as amphotericin B, compounds of the allylamine family such as terbinafine, or octopirox;

(vi) antiviral agents such as acyclovir;

(vii) steroidal anti-inflammatory agents, such as hydrocortisone, betamethasone valerate or clobetasol propionate, or nonsteroidal anti-inflammatory agents such as ibuprofen and its salts, diclofenac and its salts, acetylsalicylic acid, acetaminophen or glycyrrhetinic acid;

(viii) anaesthetics such as lidocaine hydrochloride and derivatives thereof;

(ix) anti-pruriginous agents such as thenaldine, trimeprazine or cyproheptadine;

(x) keratolytic agents such as alpha- and beta-hydroxy carboxylic acids or beta-keto carboxylic acids, their salts, amides or esters and more particularly hydroxy acids such as glycolic acid, lactic acid, salicylic acid, citric acid and fruit acids in general, and 5-n-octanoylsalicylic acid;

(xi) free-radical scavengers such alpha-tocopherol or its esters, superoxide dismutases, certain metal-chelating agents or ascorbic acid and its esters;

(xii) anti-seborrhoeic agents such as progesterone;

(xiii) anti-dandruff agents such as octopirox or zinc pyrithione;

(xiv) anti-acne agents such as retinoic acid or benzoyl peroxide;

(xv) substances and substrates such as substance P antagonists, CGRP antagonists or bradykinin antagonists or NO-synthase inhibitors or sodium-channel inhibitors, these compounds being described as being active in the treatment of sensitive skin and as having anti-irritant effects, in particular with respect to irritant compounds which may be present in the compositions;

(xvi) agents suited for modulating the skin's allergic response, such as LPV.

Active agents which can be formulated into the composition of the invention include, in particular, moisturizers such as polyols (for example glycerol), vitamins (for example D-panthenol), anti-inflammatory agents, calmants (allantoin and cornflower water), UVA and UVB screening agents, matt-effect agents (for example the partially crosslinked polydimethylorganosiloxanes marketed under the trademark KSG® by Shin-Etsu) and mixtures thereof.

Anti-wrinkle agents can also be added, and in particular tensioning products such as plant proteins and their hydrolysates, in particular the extract of soybean proteins marketed under the trademark Eleseryl® by the company LSN or the oat derivative marketed under the trademark Reductine® by the company Silab.

The present invention also features a cosmetic regime/regimen for treating skin redness and/or edema and/or sensitive skin, particularly redness and/or edema around the eyes, most particularly bags and dark rings around the eyes, comprising topically applying intimate immixture of dextran sulfate and escin, or composition comprised thereof, onto the skin.

The method or regime/regimen of the invention is a cosmetic treatment since it improves the individual's aesthetic appearance.

The cosmetic regime/regimen of the invention is advantageously carried out, in particular, by topically applying the subject compositions according to the usual technique for administering such compositions. For example: topical application of creams, gels, sera, ointments, lotions, milks, mousses, shampoos or sunscreen compositions onto the skin and/or the hair, or, alternatively, application of toothpaste onto the gums.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Study of the Anti-Edema Effect and the Vasodilation-Inhibitory Effect of Immixture of Dextran Sulfate and Escin:

The goal of this study was to visualize the anti-edema effect and the vasodilation-inhibitory effect of intimate admixture of dextran sulfate and escin, in a model of skin kept alive (eyelid) after the induction of edema and vasodilation by a neuromediator (substance P)/$\alpha$-type tumor necrosis factor (TNF$\alpha$)/arachidonic acid combination.

The comparisons below were carried out:

(a) control skin: skin with no treatment;

(b) skin subjected to the action of substance P, TNF$\alpha$ and arachidonic acid;

(c) skin subjected to the action of substance P, TNF$\alpha$ and arachidonic acid and treated with escin;

(d) skin subjected to the action of substance P, TNFα and arachidonic acid and treated with dextran sulfate;

(e) skin subjected to the action of substance P, TNFα and arachidonic acid and treated with a dextran sulfate/escin immixture.

(A) Materials and Methods:

(1) Maintenance of Human Skin Fragments Alive:

Fragments of normal human skin from 3 different donors (plastic surgery), mechanically freed of the subcutaneous fat and the inner layer of the dermis, were each placed on a culture insert consisting of a porous membrane (pores 12 μm in diameter) (Costar), the dermal portion of the skin fragment being placed in contact with the porous membrane. The assembly thus prepared was positioned over the wells of a Costar brand 12-well culture plate and maintained for 24 hours at 37° C. in an incubator under a humidified atmosphere containing 5% $CO_2$.

DMEM culture medium (Gibco-BRL) containing 100 U/ml of penicillin and 100 μg/ml of streptomycin, 200 μg/ml of L-glutamine and 0. 1% fetal calf serum (D.A.P., France), was added to the bottom of the wells such that the liquid reached the porous membrane without passing it. Thus mounted, the skin was in contact via its lower face surface through the porous membrane with the culture medium, transport taking place by slow diffusion between the two compartments.

(2) Induction of the Edema and Dilation of the Capillaries by a Combination of a Neuromediator. TNFα and Arachidonic Acid:

The edema and the vasodilation were produced experimentally by placing on the surface of the skin a mixture in a culture medium consisting of 25 μl of a neuromediator (5 μM substance P), arachidonic acid (25 μl of a solution at a concentration of 40 mg/ml in glycerol) and TNFα (50 ng/ml), hereinafter referred to as "cocktail A". These substances were maintained in contact with the skin for 2 hours.

(3) Application of the Test Products:

The test products were applied topically onto the skin fragments during the induction of the edema and the vasodilation.

The escin, at a final concentration of 0.075%, was dissolved in water.

The dextran sulfate, at a final concentration of 0.20%, was dissolved in propylene glycol.

The temperature was maintained at 37° C. throughout the test period.

(4) Histological Analysis:

The histological analyses were carried out according to the conventional techniques known to this art, without modification of the protocols.

After treatment, the skin fragments were removed and fixed in Bouin liquid and included in paraffin for the histological analyses.

After staining with hemalun-eosin, the two (2) criteria, edema and dilation of the capillaries, were evaluated by means of semi-quantitative histological scores.

The histological evaluation was carried out in the superficial dermis and in the top part of the middle dermis on the same number of fields four (4) fields at 10× magnification).

When the aspect of the capillaries or of the edema was identical for the entire section, a single score was attributed (example: score 1).

If two aspects were noted on one section, an intermediate score was attributed (example: a score of 1 to 2 is equivalent to a score of 1.5).

If the aspect was not uniform, an evaluation was made field by field and an average of all the fields was taken.

(a) Histological Evaluation of the Edema:

| Assessment | Score |
| --- | --- |
| no edema | 0 |
| very mild edema | 1 |
| moderate edema | 2 |
| considerable edema | 3 |
| very considerable edema | 4 |

(b) Histological Evaluation of the Vascular Alterations:

| Assessment | Score |
| --- | --- |
| no dilation | 0 |
| mild dilation | 1 |
| moderate dilation | 2 |
| large dilation | 3 |
| very large dilation | 4 |

(B) Results:

| | Edema | Vasodilation |
| --- | --- | --- |
| Control skin | 0.62 ± 0.63 | 0.37 ± 0.47 |
| Skin + cocktail A | 2.8 ± 0.76 | 2.2 ± 0.57 |
| Skin + cocktail A + escin | 1.16 ± 0.77 | 1.5 ± 0.5 |
| Skin + cocktail A + dextran sulfate | 2.1 ± 1.04 | 1.8 ± 1.04 |
| Skin + cocktail A + escin + dextran sulfate | 0.43 ± 0.51 | 0.5 ± 0.5 |

(a) Evaluation of the Edema:

The joint application of arachidonic acid (25 μl of a solution at a concentration of 40 mg/ml in glycerol) topically, of substance P (at a concentration of 5 μM) and of TNFα (50 ng/ml) in the culture medium generated an edema.

The increase of this edema (score of 2.8) was statistically significant (paired Student test, p<0.05) compared with the control skin for which a score of 0.62 was obtained.

The application of escin induced a decrease of this edema (score of 1.16) which was a statistically significant decrease (paired Student test, p<0.05) compared with the irritant products alone (cocktail A).

As a consequence of applying dextran sulfate, there was a tendency for this edema to decrease (score of 2.1). This decrease was not statistically significant compared with the irritant products on account of the large standard deviation.

The joint application of escin and dextran sulfate generated a decrease of the edema (score of 0.43). The results were statistically significant (p<0.05) compared with the irritant products alone (cocktail A).

Compared with the products applied separately, the application of the admixture produced a surprising synergistic effect in improving the edema score. The score obtained was in fact lower than the scores for the products used alone.

(b) Vasodilation:

The joint topical application of arachidonic acid (25 μl of a solution at a concentration of 40 mg/ml in glycerol), substance P (at a concentration of 5 μM) and TNFα (50 ng/ml) in the culture medium generated a dilation of the capillaries in the dermis.

The increase in vascular alterations (score of 2.2) was statistically significant (paired Student test, p<0.05) compared with the control skins (score of 0.37).

The application of escin induced a tendency to decrease the dilation of the capillaries (score of 1.5). This decrease was not statistically significant compared with the irritant products alone.

The application of dextran sulfate also elicited a tendency to decrease the dilation of the capillaries (score of 1.8), this decrease not being statistically significant compared with the irritant products alone.

The joint application of the products generated a decrease in the dilation of the capillaries (score of 0.5).

The results were statistically significant compared with the irritant products alone (arachidonic acid, substance P and TNFα).

Compared with the products applied separately, the application of the admixture had a surprising synergistic effect in improving the capillary-dilation score. The score obtained was in fact lower than the scores for the products alone.

(C) Conclusion:

In the model of human skin kept alive, the joint application of escin and dextran sulfate provided a surprising synergistic effect between the two (2) products with a decrease in the edema and vascular dilation induced with substance P, arachidonic acid and TNFα.

EXAMPLE 2

The following are specific examples of formulations according to the invention.

Composition 1—aqueous composition:

| | |
|---|---|
| Escin | 0.50% |
| Dextran sulfate | 0.80% |
| Water q.s. | 100% |

The water in this composition was sterile demineralized water but it can advantageously be partially or totally replaced with a spring water or mineral water such as: Eau de la Roche Posay or Eau de Vichy (Lucas source).

This composition is useful in pure or diluted form.

It can be introduced onto sterile pads, compresses or wipes to sooth the eyelids.

Composition 2—soothing wipes:

| | |
|---|---|
| Escin | 0.10% |
| Dextran sulfate | 0.20% |
| Cornflower water | 1.00% |
| Glycerol | 3.00% |
| Water q.s. | 100% |

This solution was impregnated into wipes.

It can also be incorporated into decongestion patches.

Composition 3—concentrated composition:

| | |
|---|---|
| Glycerol | 30.000% |
| Polyacrylic acid | 8.000% |
| Polysodium acrylate | 5.500% |
| Cellulose gum | 3.500% |
| Methyl paraben | 0.160% |
| Dextran sulfate | 0.160% |
| Escin | 0.030% |
| Water q.s. | 100% |

This combination can be introduced into gels or water-in-oil or oil-in-water emulsions, for eyebag-masking or ring-concealing care for the eyes. It can also be introduced into two-phase compositions or vesicular supports such as liposomes or niosomes.

Composition 4—Eyebag-masking gel:

| | |
|---|---|
| Carbomer | 0.20% |
| Acrylamide/sodium 2-acrylamidomethylpropane sulfonate/isoparaffin/water copolymer | 2.50% |
| Escin | 0.05% |
| Dextran sulfate | 0.08% |
| Sodium hydroxide | 0.05% |
| Water q.s. | 100% |

Composition 5—concealing emulsion for dark rings around the eyes:

| | |
|---|---|
| Petroleum jelly | 4.00% |
| Sorbitan tristearate | 0.90% |
| Myristyl myristate | 2.00% |
| Methyl paraben | 0.25% |
| Escin | 0.50% |
| Dextran sulfate | 1.00% |
| Eau de Vichy (Lucas source) | 5.00% |
| Water q.s. | 100% |

This composition can also be introduced into makeup products containing pigments to provide an activity on dark rings around the eyes which is both immediate, by virtue of the presence of pigments, and long-term, by virtue of the biological activity of the admixture of the invention.

Composition 6—soothing concealing emulsion for dark rings around the eyes:

| | |
|---|---|
| Petroleum jelly | 4.00% |
| Sorbitan tristearate | 0.90% |
| Myristyl myristate | 2.00% |
| Methyl paraben | 0.25% |
| Escin | 0.50% |
| Dextran sulfate | 1.00% |
| Eau de La Roche Posay | 10.00% |
| Water q.s. | 100% |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cosmetic/dermatological composition suited for treating skin redness/edema and/or sensitive skin, comprising a synergistically effective amount of comixture of escin and dextran sulfate, and a topically applicable, physiologically acceptable vehicle, diluent or carrier therefor, wherein dextran sulfate is present in an amount of from 0.08% to 1.0% by weight of said composition and escin is present in an amount of from 0.005% to 0.5% by weight of said composition.

2. The cosmetic/dermatological composition as defined by claim 1, comprising the sodium salt of said dextran sulfate.

3. The cosmetic/dermatological composition as defined by claim 1, said dextran sulfate having a molecular weight ranging from $2 \times 10^3$ to $5 \times 10^6$.

4. The cosmetic/dermatological composition as defined by claim 3, said dextran sulfate having a molecular weight ranging from $5 \times 10^3$ to $10^5$.

5. The cosmetic/dermatological composition as defined by claim 1, formulated as a gel, lotion, cream, milk, serum, paste, or mousse.

6. The cosmetic/dermatological composition as defined by claim 1, formulated as an aqueous, aqueous/alcoholic or oily solution, emulsion, dispersion, nanoparticles, or lipid vesicles.

7. The cosmetic/dermatological composition as defined by claim 1, formulated as a stick, aerosol, deodorant product, makeup product, care product, or cleaning product.

8. The cosmetic/dermatological composition as defined by claim 1, further comprising an active agent which modifies skin differentiation and/or proliferation and/or pigmentation, antibacterial agent, agent which modifies the adhesion of bacteria to the skin and/or mucous membranes, antiparasitic agent, antifungal agent, antiviral agent, steroidal or nonsteroidal anti-inflammatory agent, anaesthetic agent, anti-pruriginous agent, keratolytic agent, free-radical scavenger, anti-seborrhoeic agent, anti-dandruff agent, anti-acne agent, substance P antagonist, CGRP antagonist, bradykinin antagonist, NO-synthase inhibitor, sodium-channel inhibitor, potassium-channel opener, chlorine-channel opener, agent for modulating the allergic response of the skin, anti-wrinkle agent, or combination thereof.

9. The cosmetic/dermatological composition as defined by claim 1, further comprising a lipophilic active agent, a hydrophilic active agent, a plant hormone, a calcium antagonist, a plant extract, a microorganism extract, or combination thereof.

10. A method or regime/regimen for preventively or curatively treating skin redness and/or skin edema and/or sensitive skin, comprising administering to a candidate individual in need of such treatment, a cosmetic/dermatological composition comprising a synergistically effective amount of comixture of escin and dextran sulfate, and a topically applicable, physiologically acceptable vehicle, diluent or carrier therefor, wherein dextran sulfate is present in an amount of from 0.08% to 1.0% by weight of said composition and escin is present in an amount of from 0.005% to 0.5% by weight of said composition.

11. A method or regime/regimen for preventively or curatively treating skin redness and/or skin edema and/or sensitive skin, comprising topically applying onto the skin, mucous membranes, nails, and/or hair of a candidate individual in need of such treatment, a cosmetic/dermatological composition comprising a synergistically effective amount of comixture of escin and dextran sulfate, and a topically applicable, physiologically acceptable vehicle, diluent or carrier therefor, wherein dextran sulfate is present in an amount of from 0.08% to 1.0% by weight of said composition and escin is present in an amount of from 0.005% to 0.5% by weight of said composition.

12. A method or regime/regimen for preventively or curatively treating stinging and/or tingling of the skin and/or pruritus and/or tautness and/or heating and/or erythema, comprising topically applying onto the afflicted skin area of a candidate individual in need of such treatment, a cosmetic/dermatological composition comprising a synergistically effective amount of comixture of escin and dextran sulfate, and a topically applicable, physiologically acceptable vehicle, diluent or carrier therefor, wherein dextran sulfate is present in an amount of from 0.08% to 1.0% by weight of said composition and escin is present in an amount of from 0.005% to 0.5% by weight of said composition.

13. A method or regime/regimen for treating redness and/or edema of the skin around the eyes, comprising topically applying onto the afflicted skin area of a candidate individual in need of such treatment, a cosmetic/dermatological composition comprising a synergistically effective amount of comixture of escin and dextran sulfate, and a topically applicable, physiologically acceptable vehicle, diluent or carrier therefor, wherein dextran sulfate is present in an amount of from 0.08% to 1.0% by weight of said composition and escin is present in an amount of from 0.005% to 0.5% by weight of said composition.

14. A method or regime/regimen for treating bags and dark rings in the skin around the eyes, comprising topically applying onto the afflicted skin area of a candidate individual in need of such treatment, a cosmetic/dermatological composition comprising a synergistically effective amount of comixture of escin and dextran sulfate, and a topically applicable, physiologically acceptable vehicle, diluent or carrier therefor, wherein dextran sulfate is present in an amount of from 0.08% to 1.0% by weight of said composition and escin is present in an amount of from 0.005% to 0.5% by weight of said composition.

* * * * *